US006833494B1

(12) United States Patent
Pental et al.

(10) Patent No.: US 6,833,494 B1
(45) Date of Patent: Dec. 21, 2004

(54) REGULATION OF LETHAL GENE EXPRESSION IN PLANTS

(75) Inventors: Deepak Pental, New Delhi (IN); Arun Jagannath, New Delhi (IN); Panchali Bandyopadhyay, New Delhi (IN); Neelakantan Arumugam, New Delhi (IN); Vibha Gupta, New Delhi (IN); Pradeep Kumar Burma, New Delhi (IN)

(73) Assignees: University of Delhi, New Delhi (IN); National Diary Development Board, Gujarat (IN)

( * ) Notice: Subject to any disclaimer, the term of this patent is extended or adjusted under 35 U.S.C. 154(b) by 0 days.

(21) Appl. No.: 09/633,274

(22) Filed: Aug. 4, 2000

(30) Foreign Application Priority Data

May 30, 2000 (IN) ................................ PCT/IN00/00058

(51) Int. Cl.⁷ ........................... A10H 5/00; C12N 15/82
(52) U.S. Cl. ...................... 800/303; 800/278; 800/306; 435/320.1
(58) Field of Search ................................ 800/303, 278, 800/306; 435/320.1

(56) References Cited

U.S. PATENT DOCUMENTS 5,689,041 A * 11/1997 Mariani et al. ............. 800/205
5,977,433 A * 11/1999 Williams et al. ............ 800/274

OTHER PUBLICATIONS

Thompson et al., Characterization of the herbicide–resistance gene bar from *Steptomyces hygroscopicus* pp. 2119–2123.*
Paddon et al., Cloning, sequencing and transscription of an inactivated copy of *Bacillus amyloliquefaciens* . . . 1986. vol. 40. pp. 213–239.*
Fang et al., Multiple cis Regulatory Elements for Maximal Expression of the Cauliflower . . . Jan. 1989. The Plant Cell. vol. 1, pp. 141–150.*

Serurinck et al., The nuceotide sequence of an anther–specific gene. Apr. 24, 1990. Nucleic Acid Research. vol. 18. No. 11 p. 3403.*
Pfitzner et al., Nucleotide sequence of two PR–1 pseudogenes from *Nicotiana tabacum* cv. Wisconcin 38, 1990. Nucleic Acid Research, vol. 18, No. 11, p. 3404.*
Mariani et al., Induction of male sterility in plants by a chimaeric ribonuleases gene. Oct. 25, 1990. Nature. vol. 347, pp. 737–741.*
Mazur et al., Isolation and Characterization of Plant Genes Coding for Acetolactate Synthase. the Target Enzyme . . . 1987. Plant Physiol. vol. 85, pp. 1110–1117.*
Barnase et al., Expression of Its Cloned Inhibotor Permits Expression of a Cloned Ribonuclease. 1988. vol. 202. pp. 913–915.*
Hajdukiewicz et al., The small, vesatile pPZP family of Agrobacterium bindary vectors for plant transformation. 1994. Plant Molecular Biology, vol. 25, pp. 989–994.*
Reddy et al., Cloning, expression and cahracterization of gene which encodes a topoisomerase I with positive supercoiling activity in pea, 1998, Plant Molecular Biology, vol. 37, pp. 773–784.*
Murai, N, Accession No. X51514.*
Reddy, M.K, Accession No. Y14558.*
Mathews et al, "Transgenic plants of mustard *Brassica juncea* (L.) Czern and Coss", 1990, Plant Science vol. 72, pp. 245–252.*
Daniel, et al, "Transgenic analysis of the 5'– and 3' –flanking regions of the NADH–dependent hydroxypyruvate reductase gene from *Cucumis sativus* L.", 1995, Plant Molecular Biology vol. 28, pp. 821–836.*

* cited by examiner

*Primary Examiner*—Anne Kubelik
(74) *Attorney, Agent, or Firm*—Birch, Stewart, Kolasch & Birch, LLP

(57) ABSTRACT

The present invention relates to an Insulator construct for controlling leaky expression of a lethal gene from enhancing functions of a strong constitutive promoter present in the said Insulator construct following integration into the genome of a plant and a method for development of male sterile lines in crop plants using the said Insulator construct.

14 Claims, 5 Drawing Sheets

REGULATION OF LETHAL GENE EXPRESSION IN PLANTS

Figure 1:
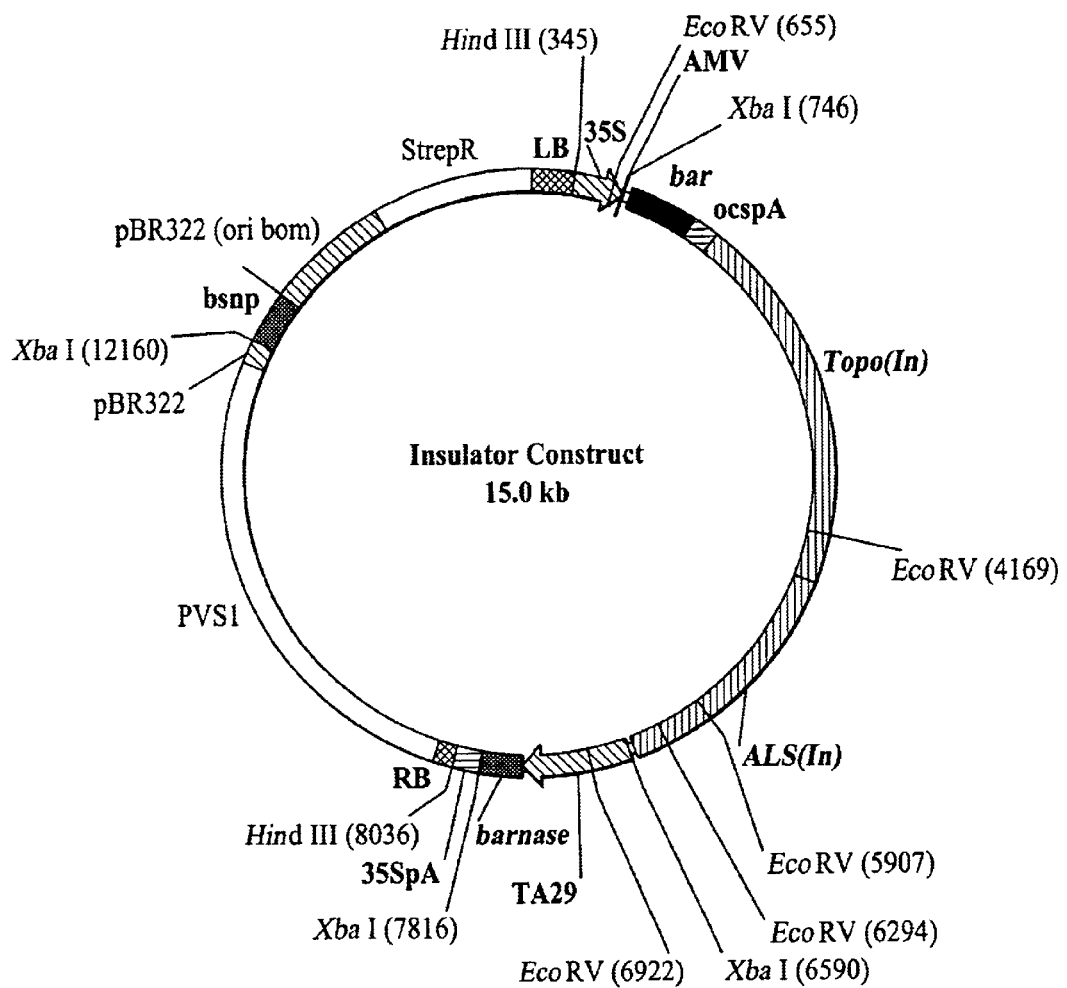

This non-provisional application claims priority under U.S.C. 119(a) PCT International Application No. PCT/IN00/00058 filed on May 30, 2000, which designated a country in addition to the United States, the entire contents of which are hereby incorporated by reference.

FIELD OF INVENTION

BACKGROUND OF INVENTION

Promoters viz. Cauliflower Mosaic Virus 35S (CaMV35S) and its variant, CaMV35S double enhancer, Figwort Mosaic Virus (FMV) and its variant, FMV double enhancer and others have been used for high level constitutive expression of heterologous genes in transgenic plant systems. The choice of a promoter is largely based on the required expression level(s) of the gene(s) under consideration. In case of marker genes, a threshold level of expression is necessary to enable selection of transgenic plants in vitro and/or in vivo. Among all homologous and heterologous promoters studied for constitutive expression of transgenes in plants, the CaMV35S and its variant, CaMV35S double enhancer promoters are known to induce significantly high levels of expression and are therefore widely used in transgenic plant research. Both these promoters are also characterized by strong enhancing functions and have been shown to induce a 40 to 50-fold increase in transcription of neighboring genes (Kay et al 1987, Science 236:1299–1302). The use of CaMV35S promoter for expression of a particular gene would therefore also influence expression of other genes present within the same transformation vector. This is of particular concern when one requires regulated expression of a gene by its transcriptional control under a tissue-specific promoter along with constitutive expression of a marker gene under transcriptional control of a strong constitutive promoter, both being located in the same DNA construct used for development of transgenic plants. Furthermore, presence of a strong promoter with enhancing effects could also lead to deceptive results in studies on temporal and spatial expression patterns of tissue-specific promoters in transgenic plant systems.

Production of male-sterile lines is important for development of hybrids in crop plants to enhance crop productivity. Use of hybrids for increasing crop yield is primarily based on utilization of the phenomenon of hybrid vigor or heterosis (Shull 1952, In Heterosis, Gowen Ed. 14–48 Ames: Iwo State College Press). Hybrid vigor has been exploited in plant breeding for several years. When two genetically diverse parents with compensatory agronomic characters are combined by conventional breeding methodologies, the F1 hybrid plants show higher yield than either of the parents [William 1959, Nature (Lond.) 184:527–530; Sinha and Khanna 1975, Adv. Agron. 27:123–174; Pradhan et al. 1993, Euphytica 69:219–229]. To produce hybrid progeny, cross-pollination must occur. However, there are several crop plants, which are naturally self-pollinating, for instance Brassica sp., rice and wheat. In the event of parental lines being self-pollinating, either the pollen-producing organ (anthers) must be removed or the male reproductive units (microspores) must be destroyed in one parent to facilitate cross-pollination. It is in this context, that the development of stable, normal male sterile lines assumes importance.

A simple method of generating a male sterile line is by physical removal of anthers (emasculation). Hybrids in maize, cotton and tomato are produced by this method. Another approach for generation of male-sterile lines for hybrid seed production is the use of cytoplasmic male sterility (CMS) systems. CMS is a maternally inherited phenomenon manifesting itself as the inability to produce functional pollen grains. The genetic determinants of male sterility in CMS systems are located in genomes of the cytoplasmic organelles, the mitochondria. Restorer genes for CMS systems are dominant nuclear genes that suppress male-sterile effects of the cytoplasm (mitochondria). When incorporated into the male parent, they can function as restorers of male fertility in the F1 hybrids. CMS systems have found widespread use in the production of hybrids in sorghum, sunflower, pearl millet and sugarbeet. However, their use has been limited in corn, wheat and oilseed Brassicas due to linkage of undesirable traits such as increased disease susceptibility, chlorosis, distortion of petals, poor nectary function, etc. with CMS in these systems (McVetty et al. 1989, Can. J. Plant Sci. 69:915–918; Burns et al 1991, Can. J Plant Sci. 71:655–661; Williams 1995, Trends Biotech. 13:344–349; Buzza 1995, In Brassica oilseeds: Production and Utilisation, Kimber and McGregor, Eds. CAB International).

With the advent of recombinant DNA and plant transformation technologies, pollination control based on genetic engineering of nuclear male sterility has emerged as a tangible option for production of male-sterile plants (reviewed by Williams 1995, Trends Biotech. 13:344–349). In these methods, the plant is provided with a male-sterility gene comprising a DNA sequence coding, for example, a cytotoxic product. The cytotoxic product, in many cases, may be a lethal gene under transcriptional control of a promoter, which is predominantly active in selective tissue(s) of the male reproductive organs in plants. As an example, male sterility could be successfully induced in transgenic tobacco and oilseed rape (*Brassica napus*) by targeted expression of a ribonuclease [barnase from *Bacillus amyloliquefaciens* (Hartley 1989, Trends Biochem. Sciences 14:450–454) or Rnase T1 from *Aspergillus oryzae*] in the tapetal tissues of anthers using a tapetum-specific promoter, TA29, from tobacco (Mariani et al 1990, Nature 347:737–741). Tapetum, which forms the innermost layers of the anther wall, is one of the most important tissues associated with pollen development. Disruption of tapetal cells by the expression of toxic proteins consequently impairs pollen development leading to male sterile plants. Several other strategies for disruption of normal pollen development have subsequently been developed (reviewed by Williams 1995, Trends Biotech. 13:344–349).

The DNA constructs used for development of male sterile lines also require the presence of a selectable marker gene(s) for in vitro selection of transformed tissues and field selection of segregants that contain the male sterility-inducing gene. Use of a strong constitutive promoter to express the marker gene is therefore important for enabling selection of transgenic plants. However, use of a strong constitutive promoter with a lethal gene in the vicinity can be detrimental to the process of generating transgenic plants using the latter because enhancing functions of the strong constitutive promoter could induce deregulated expression of the (lethal) gene that is otherwise under transcriptional control of a known tissue-specific promoter. Some DNA sequences [Scaffold or Matrix Attachment Regions (SARs/MARs)] are known to buffer, to some extent, influences of surrounding regions on transgene expression in plants (Breyne et al 1992, Plant Cell 4:463–471, Mlynarova et al 1994, Plant Cell 6:417–426, Mlynarova et al 1996, Plant Cell 8:1589–1599). However, SARs are also known to possess enhancing functions (Steif et al 1989, Nature 341:343–345, Allen et al 1993, Plant Cell 5:603–613). Use of such sequences to achieve conditional expression of lethal genes is therefore not advisable.

Plant Genetic Systems have described, in EP 0344029A1, use of the barnase gene for generation of male-sterile lines for hybrid seed production. According to this patent, the barnase construct used for plant transformation contained three components:
1. a male sterility-conferring transcription unit (TA29 promoter-barnase gene),
2. a nos promoter-nptII marker gene cassette: the nptII gene encodes the enzyme neomycin phosphotransferase which confers resistance to the antibiotic, kanamycin and can therefore be used for in vitro selection of transformed tissues, and
3. a rbcs promoter-bar marker gene cassette: the bar gene (from *Streptomyces hygroscopicus*) encodes the enzyme phosphinothricin acetyl transferase which confers resistance to the herbicide, Basta. It can therefore be used for field selection of lines with the male sterility-conferring gene among segregants. The rbcs promoter used in the above construct was isolated from Arabidopsis and regulates expression of the rubisco small subunit gene in the same.

Although the above patent claims capability of in vitro selection of transformed tissues on the herbicide, it is known that the rbcs promoter is highly active only in green tissues of intact plants. Its activity in iii vitro grown callus tissues is very low. Hence, it might be inadequate for in vitro selection of transgenic plants on the selective agent i.e. herbicide. The strategy described in the above patent envisages the use of two different marker genes, one primarily for in vitro selection (nptII) and another for field selection (bar). Keeping in mind the general reluctance to accept marker genes conferring resistance to antibiotics, the presence of nos-nptII in the transgenic lines is superfluous. Further, there is no information in the said patent on transformation frequencies of plants obtained using the barnase gene or other constructs containing any other lethal gene. Therefore, the ease of developing transgenic plants with conditional expression of lethal genes has not been described. Moreover, the barnase gene construct described in the above patent does not envisage the need for the inhibitor gene, barstar in the background (as evidenced in this study and by Paul et al 1992, Plant Mol. Biol. 19:611–622). Barstar is an inhibitor protein produced by the bacterium, *Bacillus amyloliquefaciens*, wherein it negates the lethal effects of the ribonuclease by forming a one-to-one complex with the same in the cytoplasm (Hartley and Smeaton 0.1973, J. Biochem. 248:5624–5626).

Forbio Research Pvt. Ltd. in WO9730162A1 has described a method for protecting tissues from leaky expression of barnase gene by using coordinated expression of two additional components. One of these components is the inhibitor gene, barstar under transcriptional control of a modified CaMV35S promoter containing the repressor-binding site (operator) of the lac operon of the bacterium, *Escherichia coli*. Expression of the barstar gene, in turn is regulated by a second modulator gene encoding the repressor of the lac operon (lacIq) expressed under the same tissue-specific promoter as the barnase gene. The above strategy is a multi-component, multi-functional system, which necessitates proper functionality of each component. Any variation in expression of the same can render the entire system non-functional. Moreover, the strategy also envisages the use of many redundant genes and promoters, the presence of which is undesirable in agronomic applications of the said technology.

Plant Genetic System, in a subsequent U.S. Pat. No. 6,025,546, has described another strategy for development of male sterile plants in corn, rice and oilseed rape (*Brassica napus*) using the barnase gene under transcriptional control of appropriate tapetum-specific promoter(s). This patent also describes use of the inhibitor gene, barstar as a co-regulator for development of male sterile lines. Further, it highlights the need to clone the barstar gene in the background of all barnase-containing vectors. The barstar gene is preferentially placed under transcriptional control of a constitutive promoter (for example, CaMV35S promoter) to negate any undesirable effects on transformed tissues due to leaky expression of the barnase gene. The co-regulating gene (barstar) may be located in the same transformation vector containing the barnase gene or may be used independently in co-transformation experiments. In addition, the applicants of this patent describe yet another strategy involving deployment of the barstar gene under control of a minimal promoter in order to utilize enhancing functions of plant enhancers. According to the patent, these strategies would not only be effective in countering leaky expression of the barnase gene due to position effects but would also increase the frequency of male sterile plants exhibiting good agronomic performance. Although the patent highlights the fact that the described strategy could be used for any sterility-inducing DNA, it follows that such a strategy would be effective only in situations wherein a corresponding inhibitor protein is known for the male-sterility gene.

Problems associated with leaky or deregulated expression of tissue-specific promoters in the presence of a strong constitutive promoter are, therefore, a major impediment to targeted expression of genes in specific tissues. The present invention addresses the above issue without the involvement of any co-regulating gene or other functional component(s). Further, it facilitates development of strategies for producing stable and normal male sterile lines at high frequencies to exploit the development in genetic engineering technologies and genomic research for improving yields of crop plants. The present invention provides a strategy for protecting tissue-specific expression using one of the strongest constitutive promoters and one of the most potent lethality-inducing genes known to date merely as an example. The strategy involves use of a DNA sequence, hereinafter referred to as "Insulator", which distances the strong constitutive promoter from the tissue specific promoter in a construct used for development of transgenic plants. The efficacy of the strategy would be applicable to any other sequence combination with similar properties in transgenic plants.

OBJECTS

The main object of the invention is to provide a novel Insulator construct for protecting tissue-specific expression of a lethal gene from enhancing functions of a strong constitutive promoter located in the vicinity thereof.

Another object is to develop a construct for controlling leaky expression of a lethal gene, said construct containing a single selectable marker gene for in vitro as well as field-level selection of transgenic plants.

A further object is to develop a construct that can be used for controlling leaky expression of a lethal gene without the involvement of any other regulatory or inhibitor sequence component.

Another object is to develop a construct that would confer protection against leaky expression of a lethal gene over all the developmental stages of a plant.

Yet another object is to develop normal, stable male sterile lines generated at a high frequency by genetic transformation using constructs developed according to the invention to protect tissue-specific expression of a lethal gene.

Still another object is to provide methods for developing normal, stable male sterile lines generated at a high frequency in crop plants using the Insulator construct of the invention.

SUMMARY OF INVENTION

The invention provides a novel Insulator construct for controlling leaky expression of a lethal gene from enhancing functions of a strong constitutive promoter present in the said Insulator construct following integration into the genome of a plant, said construct comprising (i) a first transcription unit containing a lethal gene under transcriptional control of a tapetum-specific promoter and fused to a suitable transcription termination signal including a polyadenylation signal, (ii) a second transcriptional unit comprising a selectable marker gene, under transcriptional control of a strong constitutive promoter with a leader sequence and fused to a suitable transcription termination signal, including a polyadenylation signal and (iii) an Insulator sequence placed between the first and second transcription units, so as to distance the first transcription unit from enhancing functions of the constitutively expressing promoter in the second transcription unit. Further, the invention provides a method for development of stable, normal male sterile lines using the Insulator construct, the said method comprising a series of checks or "sieves" to test for protected tissue-specific expression of the lethal gene in the presence of the strong constitutive promoter. The said method comprises the steps of testing transformation and regeneration frequencies, development of male sterile transgenic plants, analysis of vegetative morphology and female fertility of male sterile plants, Southern analysis for identification of male sterile plants containing a single copy of the T-DNA insert, analysis of germination frequencies and segregation data of T1 seeds and stable inheritance of male sterility in T1 progeny.

DETAILED DESCRIPTION OF INVENTION

The present invention relates to an Insulator construct for controlling leaky expression of a lethal gene from enhancing functions of a strong constitutive promoter present in the said Insulator construct following integration into the genome of a plant and a method for development of male sterile lines in crop plants using the said Insulator construct.

Accordingly, the invention provides an Insulator construct comprising:

i) a first transcription unit comprising a lethal gene under transcriptional control of a tissue specific promoter for targeted expression in specific tissue(s) and fused to a suitable transcription termination signal, including a polyadenylation signal, ii) a second transcription unit comprising a selectable marker gene under transcriptional control of a strong constitutive promoter with a leader sequence and fused to a suitable transcription termination signal, including a polyadenylation signal, and iii) an Insulator sequence placed between the first and second transcription units so as to distance the first transcription unit from enhancing functions of the constitutively expressing promoter in the second transcription unit.

In an embodiment, the lethal genes that can be used in the Insulator construct could be any coding sequence which, when expressed in a cell (as RNA or protein), significantly disrupts the normal metabolism, functioning or development of any such cell, preferably leading thereby to death of the cell. Instances of such lethal genes include ribonucleases such as RNAseT1 (from *Aspergillus oryzae*), barnase (from *Bacillus amyloliquefaciens*), binase (from *Bacillus intermedius*); rol genes from *Agrobacterium rhizogenes*; diphtheria toxin A chain-encoding gene etc. In a preferred embodiment, the lethal gene used in the Insulator construct is the ribonuclease gene, barnase derived from the bacterium *Bacillus amyloliquefaciens*.

Tissue specific promoters are characterized by definite temporal and spatial expression patterns during plant growth and development. A large number of such promoters are known in plant systems. A few examples include anther specific promoters such as TA29, A9, tap1, bcp1 or seed specific promoters such as napin. In an embodiment the tissue specific promoter used to express the barnase gene is the tapetum-specific promoter TA29.

A selectable marker gene encodes a RNA or protein which, when expressed in the cells of the plant, gives the cells expressing the gene a selective advantage over cells lacking the same. In an embodiment, the marker gene is selected from the group of herbicide resistance-conferring genes such as bar, tfdA, ALS; antibiotic resistance-conferring genes such as nptII, hpt, aadA, etc. In a preferred embodiment of the invention, the selectable marker gene used for in vitro and in vivo selection of transformed tissues is the herbicide resistance conferring gene, bar from *Streptomyces hygroscopicus*.

In an embodiment, the promoter used for driving the expression of the bar gene is the CaMV35S promoter, which is a known strong constitutive promoter.

A leader sequence of the Alfalfa Mosaic Virus (AMV) RNA4 gene has been incorporated in the above constructs between the CaMV35S promoter and the bar gene. Such leader sequences are known to enhance expression levels by improving translational efficiency without influencing promoter strength (Gallie et al 1987, Nucl. Acids Res. 15:8693–8711, Day et al 1993, Plant Mol. Biol. 23:97–109).

The transcription unit of the selectable marker gene is placed towards the Left Border of T-DNA (in an appropriate binary vector) to ensure complete transfer of all components located between the T-DNA borders during Agrobacterium-mediated genetic transformation.

The Insulator sequence comprises a sequence derived from genomic DNA of a plant. It does not encode any functional RNA or protein but when placed between the two transcription units of the Insulator construct, serves to substantially negate the deleterious effects resulting from leaky expression of the lethal gene due to enhancing functions of the strong constitutive promoter. While there are no limitations as to the sequence per se that can be used as an Insulator, it is recommended that a sequence with the following properties be selected:

i) The Insulator sequence should not bear strict homology with any component of the host genome in order to avoid, to the maximum extent possible, induction of homology-dependent gene silencing (reviewed in Meyer and Saedler 1996, Ann. Rev. Plant Physiol. Plant Mol. Biol. 47:23–48).

ii) GC content of the Insulator sequence should be in consonance with transcriptionally active regions of the host genome.

iii) The Insulator sequence should not encode any functional or regulatory component nor possess any regulatory or enhancer elements or sequences that may influence expression of neighboring genes.

In still another embodiment, the Insulator sequence comprises a DNA sequence generated from partial coding sequences of two dicot genes (a topoisomerase gene from pea and an acetolactate synthase gene from Arabidopsis).

The length of the Insulator sequence used in the Insulator construct would vary according to the nature and strength of the constitutive promoter used. The optimum length of the Insulator sequence is governed by the primary objective of generating a large number of normal male sterile plants. It is recommended that the Insulator sequence may have a length of at least 2 kb. In a preferred embodiment, the Insulator sequence has a length of about 5 kb.

DNA vector(s) containing the barnase gene also have the barstar gene transcribed by its native bacterial promoter cloned in the vector backbone. This was necessitated because of the inability to clone the barnase gene in the absence of background levels of the Barstar protein. The binary vector, pPZP200 (Hajdukiewicz et al 1994, Plant Mol. Biol. 25:989–994), was used as the transformation vector.

The invention also provides a method to obtain normal male-sterile plants at a high frequency. The said method incorporates a series of checks or "sieves" to test for protected tissue-specific expression of the lethal gene in the presence of the strong constitutive promoter. The said sieves are primarily identified and selected for on the basis of their role in determining the agronomic viability of any (transgenic) crop plant and are as outlined below:
i) frequency of genetic transformation and regeneration
ii) vegetative morphology of transgenic male sterile plants
iii) female fertility of transgenic male sterile plants
iv) germination frequencies of T1 seeds obtained by backcrossing transgenic male sterile plants
v) segregation ratios of marker gene/male sterility among T1 plants
vi) stable inheritance of male sterile phenotype among T1 plants.

The said method for the development of male sterile plants comprises the steps of:
i) transforming the nuclear genome of plant cells with an Insulator construct comprising:
   a) a first transcription unit comprising a lethal gene under transcriptional control of a tissue specific promoter for targeted expression in specific tissue(s) and fused to a suitable transcription termination signal, including a polyadenylation signal,
   b) a second transcription unit comprising a selectable marker gene under transcriptional control of a strong constitutive promoter with a leader sequence and fused to a suitable transcription termination signal, including a polyadenylation signal,
   c) an Insulator sequence placed between the first and second transcription units so as to distance the first transcription unit from enhancing influences of the constitutive promoter in the second transcription unit.
ii) regenerating plants from said transformed plant cells,
iii) identification of male sterile transgenic plants by morphological observations and by their failure to set seed on selfing,
iv) obtaining, at a high frequency, male sterile plants with normal vegetative morphology and normal female fertility,
v) identifying single copy male sterile lines by Southern hybridization,
vi) back-crossing male sterile plants with untransformed parent to obtain T1 seeds,
vii) obtaining male sterile plants with normal T1 seed germination frequencies,
viii) obtaining normal segregation ratio of marker gene among T1 progeny of single copy male sterile plants identified,
ix) obtaining stable transfer of male sterile phenotype among all T1 plants exhibiting marker resistance.

In an embodiment, the preferred lethal gene is barnase.

In still another embodiment, the preferred tissue specific promoter is TA29.

In yet another embodiment, the preferred marker gene is bar.

In another embodiment, the preferred constitutive promoter is CaMV35S promoter.

In an embodiment, the Insulator sequence has a length of about 5 kb.

In an embodiment, the crop plants used for genetic transformation are selected from dicotyledonous plants, such as *Brassica juncea*.

In another embodiment, the procedure used for development of transformed plants in *Brassica juncea* is Agrobacterium-mediated transformation using disarmed Ti plasmid.

In an embodiment, the transgenic male-sterile plants are scored for abnormalities in vegetative characters In another embodiment, the male sterile transgenic plants are backcrossed to the untransformed parent and tested for female fertility.

In another embodiment, the male sterile plants are analyzed by Southern hybridization to identify transgenic plants containing a single copy of the T-DNA insert.

In yet another embodiment, seeds obtained from back-crossing the above male sterile plants are tested for their viability as evidenced by their ability to germinate on non-selective media.

In still another embodiment, germinated seedlings obtained from backcrossed seeds were tested for segregation of the marker gene by transferring them on selective media.

In another embodiment, the T1 plants obtained from selected backcrossed progeny were transferred to field conditions and tested for stable inheritance of the male sterile phenotype.

The invention is described in detail hereinafter, with reference to the accompanying drawings and examples. Various modifications, especially with respect to the Insulator construct and the methods used to deploy the same would be obvious to those skilled in the art. Such modifications are deemed to fall within the scope of the present invention and the examples and embodiments provided herein should not be construed as limitations on the inventive concept embodied in this invention.

BRIEF DESCRIPTION OF THE ACCOMPANYING DRAWINGS

In the drawings that accompany,

FIG. 1: is a schematic representation of the Insulator construct depicting various components and locations of restriction enzyme sites. Abbreviations: LB—Left Border of T-DNA of *Agrobacterium tumefaciens*, RB—Right Border of T-DNA of *Agrobacterium tumefaciens*, AMV—Leader sequence of Alfalfa Mosaic Virus, Topo(In)— Topoisomerase gene component of Insulator sequence, ALS (In)—acetolactate synthase component of Insulator sequence, Bsnp—barstar gene transcribed by its native bacterial promoter, 35S—CaMV35S promoter, 35SpA— polyadenylation signal of Cauliflower Mosaic Virus, ocspA-polyadenylation signal of octopine synthase gene.

Figure 2A:

FIGS. 2a,b: are photographs depicting flowers (a) in an inflorescence of male sterile transgenic plants generated using the Insulator construct (b) in an inflorescence of an untransformed parent.

Figure 3A:
Figure 4A:
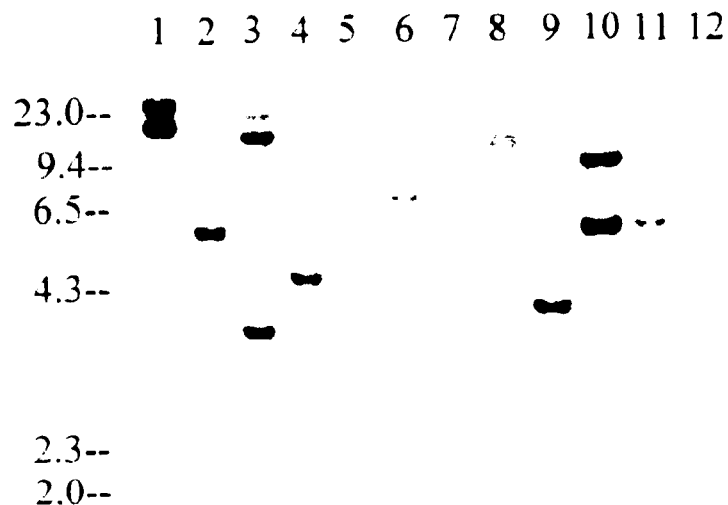
Figure 4B:
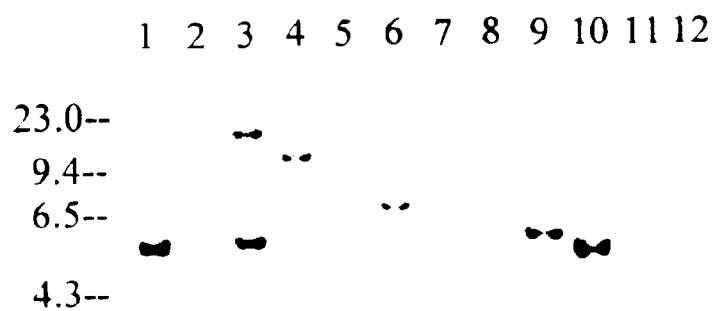

FIGS. 3a,b: are photographs depicting vegetative morphology of male sterile plants. (a) healthy male sterile plant (b) chlorosis and puckered leaves in an abnormal male sterile plant FIGS. 4a,b: are photographs depicting Southern hybridization analysis of a representative population of male sterile plants (11 nos.) obtained from transformation experiments using the Insulator construct. (a) Copy number on the left border flank was determined by probing EcoRI digests of genomic DNA with coding sequence of the bar gene. (b) Copy number on the right border flank was determined by probing EcoRI digests of genomic DNA with coding sequence of the barnase gene. Lanes 1–11 represent male sterile barnase plants while lane 12 represents an untransformed control plant. The numbers along the left margin of FIG. 4 represent a non-linear scale, in kilobase pairs (kb), of DNA fragment sizes.

Figure 5:
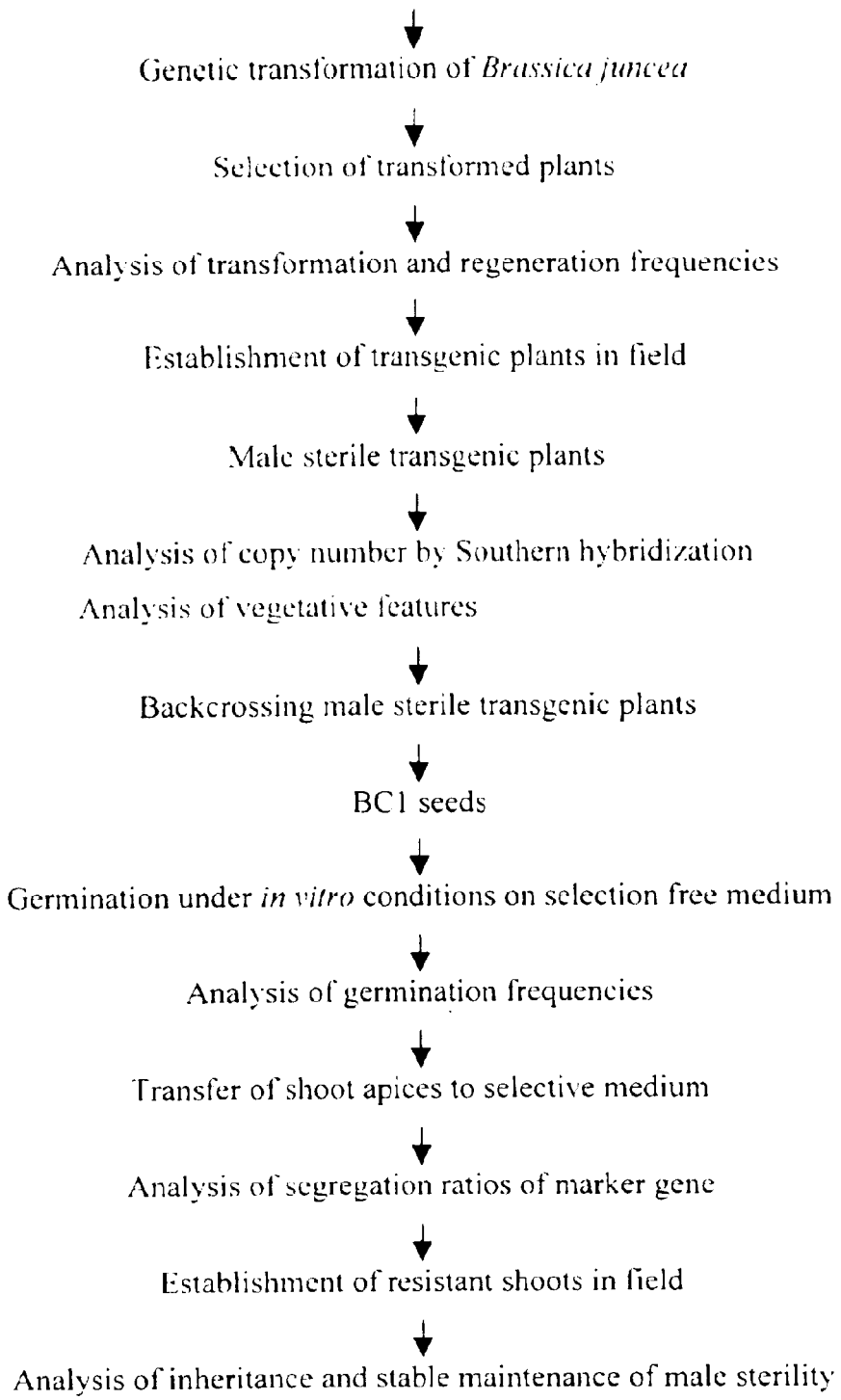

FIG. 5: is a schematic flow diagram describing the methodology used to test efficacy of the Insulator construct and development of male sterile plants in *Brassica juncea*. It comprises the steps of testing transformation frequency, development of male sterile transgenic plants, analysis of vegetative morphology and female fertility of male sterile plants, Southern analysis for identification of male sterile plants containing a single copy of the T-DNA insert, analysis of germination frequencies and segregation data of T1 seeds and stable inheritance of male sterility in T1 progeny.

To discuss in detail, the invention involves transformation of a plant cell using the Insulator construct of the invention comprising the lethal gene under the control of a tissue specific promoter, a marker gene under the control of a strong constitutive promoter and a fragment of plant genomic DNA placed between the transcription units as described in the foregoing sections. A schematic representation of the Insulator construct is shown in FIG. 1 of the accompanying drawings. The said transformation can be carried out employing various vectors and well established procedures such as PEG-mediated direct gene transfer and Electroporation (Bilang et al 1994, In Plant Mol. Biol. Manual, Gelvin and Schilperoot, Eds. Kluwer Academic Publishers), Particle Bombardment (Christou 1994. Plant Mol. Biol. Manual, Gelvin and Schilperoot, Eds. Kluwer Academic Publishers), Agrobacterium-mediated transformation using disarmed Ti-plasmid vectors (Plant Mol. Biol. Manual, Gelvin and Schilperoot. Eds. Kluwer Academic Publishers), etc. The applicants recommend the use of Ti-plasmid vectors for genetic transformation of plants because of better control over the process of gene transfer and selection of transgenic plants. In cases of Agrobacterium-mediated transformation using disarmed Ti-plasmid vectors, the marker genes are preferably located towards the left border sequence of T-DNA so as to enable selection of transformants carrying the complete T-DNA.

The lethal gene, the tissue specific promoter, the marker gene, the promoter expressing the marker gene and the Insulator sequence can be used in a variety of plants to induce male sterility. The Insulator construct is transformed into *Brassica juncea* by Agrobacterium-mediated transformation. Transgenic shoots are selected on 10 mg/L of phosphinothricin (selective agent for the bar gene). Transformation frequencies are calculated as a percentage of number of explants regenerating over number of explants inoculated on appropriate selective media. The Insulator construct gives a transformation frequency of 3.5% (168 explants regenerating of 4769 explants inoculated) whereas an identical construct minus the Insulator sequence gives a much lower transformation frequency of 0.9% (82 explants regenerating of 8206 explants inoculated). The transformed shoots obtained above are transferred to a rooting medium to obtain complete transformed plants, which are subsequently transferred to field conditions and grown to maturity.

Figure 2B:
Figure 3B:

Male-sterile lines obtained using the above constructs are characterized by the presence of rudimentary and flattened anthers in flowers with complete absence of pollen production in contrast to flowers of untransformed plants. As shown in the accompanying drawings, FIG. 2(a) depicts flowers in the inflorescence of male sterile plants and FIG. 2(b) depicts the flowers in the inflorescence of untransformed plants. Close monitoring of male sterility over a period of two months of flowering revealed no breakdown of sterility among the male-sterile lines indicating complete functionality and stable expression of the lethal gene. The effects of the lethal gene on other aspects of plant development viz., vegetative morphology and female fertility were also analyzed. Vegetative abnormalities viz., chlorosis, stunted growth and puckered leaves are absent among male sterile transgenic plants generated using the Insulator construct as shown in FIG. 3(a) but are encountered frequently among male-sterile transgenic plants raised using an identical construct minus the Insulator sequence as shown in FIG. 3(b).

All male-sterile plants generated using the Insulator Construct set proper seed in backcrosses. However, most plants generated using an identical construct minus the Insulator sequence failed to set seed in backcrosses and seed set was poor in the rest with most seeds being shriveled.

Transgenic plants containing a single copy of the T-DNA insert were identified by Southern hybridization as shown in FIGS. 4(a) and (b) and backcrossed to the untransformed parent for further analysis.

Backcrossed seeds of single-copy male sterile transgenic plants were germinated on selection-free medium to study percent germination of transgenic seeds. Transgenic plants raised using the Insulator construct showed a consistently high germination frequency of >85% for a majority of events. However, transgenic plants raised using a identical construct minus the Insulator sequence showed poor germination frequencies, with 60% of transgenic plants showing germination frequencies of <40%. This might be attributed to leaky expression of the lethal gene during germination of backcrossed seeds derived from plants generated using the construct minus the Insulator sequence. Upon transfer to selection medium, ~90% of backcrossed seedlings from transgenic plants generated using the Insulator construct segregated in the expected 1:1 ratio of resistance: sensitivity to the selective agent, phosphinothricin. However, none of the transgenic seedlings derived from the construct minus the Insulator sequence showed the expected 1:1 segregation. These results clearly demonstrate efficacy of the Insulator sequence in preventing leaky expression of the lethal gene over all stages of the life cycle of a plant.

Further, all T1 plants transplanted under field conditions demonstrated complete male sterility thereby indicating stable transfer of the male sterile phenotype over sexual cycles.

The complete methodology used to test the efficacy of the Insulator construct in the development of male sterile plants in *Brassica juncea* is schematically represented in FIG. 5.

It is important to note that the seeds obtained from the transformed plant contain the Insulator construct as a stable genomic insert. Thus, the male-sterility gene, when introduced into a particular line of a plant species can be easily introduced into any other line by backcrossing. The present invention thus provides a successful strategy for protecting tissue specific expression of lethal genes in plant systems. Further, it also provides a method for routine development of male sterile lines with high agronomic value in crop plants for hybrid seed production.

EXAMPLES

Example 1
Development of Insulator Construct:
a) Amplification of TA29 promoter:
   Primers were designed to amplify the tapetum-specific TA29 promoter from tobacco genomic DNA by Polymerase Chain Reaction (PCR). The amplified fragment included 50 bp downstream to the +1 site comprising the 5' untranslated leader and the ATG start codon of the TA29 gene. Overhangs with suitable restriction sites were incorporated in the 5' ends of primers to facilitate downstream subclonings. Following PCR amplification using Amplitaq DNA polymerase (Perkin Elmer), the PCR product was gel purified, blunt-ended using PCR Polish Kit (Stratagene) and mobilized into appropriate cloning vectors.
b) The aforementioned TA29 promoter was used to drive expression of the barnase gene which was fused at its 5' end with the said promoter at an NcoI site and at its 3' end with a transcriptional termination/polyadenylation signal at an XbaI site.
c) The bar gene was used as a plant selectable marker, for which purpose, it was fused at its 5' end with a strong constitutive promoter (CaMV35S) along with a leader sequence from the Alfalfa Mosaic Virus (AMV). A suitable transcription termination/polyadenylation signal was fused with the said gene at its 3' end.
d) The Insulator sequence components, comprising partial coding regions of topoisomerase gene from pea and acetolactate synthase gene from Arabidopsis, were cloned at NdeI-BglII and NcoI-XbaI sites respectively of the plasmid vector pMCS5 (Hoheisel 1994, Biotechniques 17:456–460).
e) The components described in (a) to (d) were mobilized into the binary vector pPZP200 as described below:
   The TA29-barnase-pA transcription unit was cloned at the HindIII restriction site of the above binary vector followed by cloning of the CaMV35S-AMV-bar-pA transcription unit as a SnaBI-StuI fragment at a blunt-ended EcoRI site of the same. The Insulator sequence was mobilized as a SwaI-PmeI fragment into the StuI-EcoRI (blunt-ended) sites of the above vector containing the said transcription units.
f) The final transformation vector was mobilized into Agrobacterium tumefaciens strain GV3101 by electroporation using the BioRad Gene Pulser according to manufacturers' instructions.

Example 2
Seed Sterilization and Germination:
Seeds were surface sterilized by treatment in diluted Teepol solution (laboratory grade surfactant) for 10 minutes followed by washing under running water for 30 minutes. Seeds were subsequently treated with 70% ethanol for two minutes under sterile conditions and rinsed twice with sterile distilled water. Further, seeds were treated with 0.05% mercuric chloride for 10 minutes followed by a treatment with 1% w/v sodium hypochlorite for 9 minutes. Following each treatment, seeds were rinsed thoroughly with sterile distilled water. Surface sterilized seeds were germinated on hormone-free full strength MS medium (Murashige and Skoog 1962, Physiol. Plant. 15:473–493). Seeds were germinated in glass tubes covered with a cotton plug with four seeds in each tube. The seeds were kept in dark for two days and then maintained under light (Philips cool-white fluorescent lamps, 2000 lux, 16-h light/8-h dark cycle). Temperature in the culture room was maintained at 23±1° C.

Example 3
Agrobacterium-Mediated Genetic Transformation of Brassica juncea:
Transformation of Brassica juncea was performed according to the protocol described by Bade and Damm (1995, In Gene Transfer to Plants. Potrykus and Spangenberg, Eds. Springer Lab Manual) with further modifications. A single bacterial colony harboring the desired construct was inoculated in selective medium containing appropriate antibiotics and grown to saturation. A secondary culture was initiated from the saturated primary culture and grown for 3 hours at 28° C. in non-selective medium. The bacterial cells were subsequently harvested by centrifugation at 5000 rpm for 15 min at 22° C. and resuspended to a final $OD_{600}$ (optical density at 600 nm wavelength) of 0.3 in MS medium containing plant growth hormones, 1 mg/ml BAP (6-benzylaminopurine) and 1 mg/ml NAA (α-naphthalene acetic acid). This suspension was used for infection of explants. Hypocotyls of five-day old seedlings of Brassica juncea (germinated on an appropriate medium as described above in Example 2) were cut into 5 mm long segments and precultured in aforementioned medium (hereinafter referred to as MSN1B1) for 18 hours at 22° C. with mild shaking at 110 rpm. Following preculture, the medium was decanted and explants were infected for 30 minutes with the bacterial suspension prepared as described earlier. The bacterial suspension was then replaced with MSN1B1 medium and the hypocotyl explants were cultured for 12–14 hours under similar conditions as described above. The explants were subsequently washed with MSN1B1 containing 200 mg/L of the bacteriostatic agent augmentin (to restrict growth of Agrobacterium) and plated on appropriate selective media [MSN1B1+phosphinothricin (10 mg/L)]. Regenerated shoots were transferred after six weeks to MS medium containing 2 mg/L IBA (Indole 3-Butyric Acid) for rooting and were maintained as nodal cultures until transplantation.

Example 4
Molecular Characterization of Male-Sterile Transgenic Plants:
(a) Isolation of total DNA:
   Total DNA was isolated from fully expanded leaves of transgenic plants (growing in the field under containment conditions) and the untransformed parents following Rogers and Bendich (1994, In Plant Mol. Biol. Manual, Gelvin and Schilperoot, Eds. Kluwer Academic Publishers). One gram of leaf tissue was finely powdered in liquid nitrogen and homogenized in 5 ml extraction buffer containing 100 mM Tris-HCl pH 8.0, 20 mM Sodium EDTA (ethylene diamine tetraacetic acid) pH 8.0, 1.4M Sodium Chloride, 1% PVP40 (polyvinyl pyrrolidone 40) and 2% CTAB(Cetyltrimethylammonium bromide). The above material was incubated at 65° C. with occasional shaking followed by extraction with an equal volume of chloroform: isoamylalcohol. To the supernatant obtained above, 1.25 ml of 10% CTAB solution was added followed by extraction with an equal volume of chloroform: isoamylalcohol. Genomic DNA was precipitated from the above supernatant by addition of three volumes of precipitation buffer (50 mM Tris-HCl pH 8.0, 10 mM Sodium EDTA and 1% CTAB) followed by incubation at room temperature for 30 minutes. The pellet obtained was dissolved in 500 µl of buffer containing 10 mM Tris-HCl pH 8.0, 1 mM Sodium EDTA and 1M NaCl. Undissolved impurities were removed from the above sample by centrifugation followed by precipitation of dissolved DNA using 100% ethanol. The DNA pellet was washed with 70% ethanol and finally dissolved in an appropriate amount of sterile distilled water.

(b) Protocols for Restriction Digestion and Southern Hybridization:

Ten micrograms of total genomic DNA were digested overnight with appropriate restriction enzyme(s) in a 70 µl reaction volume containing 40 units of the restriction enzyme under conditions as recommended by the manufacturers. The digested DNA was electrophoresed on a 0.8% agarose gel at 1.75V/cm for 18–20 hours. Following electrophoresis, the restricted DNA was transferred onto a nylon membrane (Hybond N+, Amersham) by capillary action (for 12–14 hours), air-dried for 45 min and cross-linked in a UV-Crosslinker (Amersham) at $7 \times 10^4$ joules/$cm^2$. Probes used for hybridization were labeled with $\alpha$-$^{32}$PdCTP or $\alpha$-$^{32}$PdATP by a random priming method using the Megaprime DNA Labeling System (Amersham Pharmacia Biotech). Following hybridization, blots were washed twice in 2×SSC buffer (30 mM sodium chloride and 0.3M sodium citrate, pH 7.6) at 25° C. for 15 min each, followed by one wash at 65° C. for 15 minutes. Stringent washes (wherever necessary) were performed in 0.2×SSC, 0.1% SDS at 65° C. for 15 minutes. The blots were subsequently covered with saran wrap and exposed to X-ray films (Kodak) for 12–24 hours at minus 80° C. Prior to reprobing, blots were deprobed for 40 min in 0.4N NaOH at 42° C. followed by treatment with a neutralization solution (0.2M Tris pH 8.0, 0.1×SSC, 0.5% SDS) for 40 minutes at 42° C.

(c) Analysis of Copy Number:

Transgenic male-sterile plants of *Brassica juncea* were subjected to Southern hybridization to determine copy number of the T-DNA insert and to identify single-copy plants for further analysis. Genomic DNA isolated from leaves of transgenic plants was digested with the restriction enzyme EcoRI and electrophoresed on a 0.8% agarose gel. Following electrophoresis, the restricted DNA was transferred onto a nylon membrane and cross-linked using a UV-crosslinker. The southern blots thus generated were probed with the coding sequences of bar and barnase genes (representing DNA sequences derived from both sides of the restriction enzyme site(s) used above) in order to analyze copy number on both flanks of the T-DNA.

Example 5

Segregation Analysis and Seed Germination Frequencies:

T1 seeds obtained by backcrossing single-copy transgenic male-sterile plants identified above were analyzed for their germination frequencies in order to test the viability of transgenic seeds. Seeds were surface-sterilized and inoculated on non-selective media according to procedures described in Example 2. Seed germination frequency for each single-copy male-sterile plant was calculated as a percentage of the ratio of number of seeds germinated over number of seeds inoculated. The apices of germinated seedlings were sub-cultured on selective media (containing 10 mg/L phosphinothricin). Segregation ratios were calculated in terms of resistance (R)/sensitivity (S) to the selective agent (phosphinothricin).

ADVANTAGES 1) the present invention provides a combination of a strong constitutive promoter (CaMV35S), tissue-specific promoter (TA29), selectable marker gene (bar) and lethal gene (barnase) in a novel construct called the insulator construct that can be used for the development of normal stable male sterile lines in *Brassica juncea* at a high frequency by protecting tissue specific expression of the lethal gene from enhancing functions of the strong constitutive promoter.

2) the insulator construct provides protection against leaky expression over all stages of development of a plant thereby facilitating generation of agronomically viable male sterile systems in crop plants for hybrid seed production.

3) the present strategy does not require prior knowledge of any inhibitor protein or any other regulatory component of the lethal gene to achieve protection against leaky expression of the lethal gene in transgenic plants.

4) the insulator construct negates the use of any additional functional regulatory or inhibitory component to achieve protection against leaky expression of the lethal gene in transgenic plants with the insulator sequence functioning as a purely structural entity.

5) the insulator construct provides the ability to use a single selectable marker gene for in vitro as well as in vivo selection of transgenic plants.

6) the efficacy of the present invention has been tested extensively using one of the strongest constitutive promoters and one of the most potent lethal genes known till date and can therefore be extrapolated to any other combination of constitutive promoter/lethal gene in other crop plants.

What is claimed is:

1. An insulator construct for reducing leaky expression of a lethal nucleic acid caused by a strong constitutive promoter, wherein the insulator construct comprises:

(i) a first transcription unit comprising in operable linkage: a tapetum specific promoter, a lethal nucleic acid and a transcription termination sequence, wherein said transcription termination sequence comprises a polyadenylation sequence;

(ii) a second transcription unit comprising in operable linkage: a strong constitutive promoter, a selectable marker nucleic acid and a transcription termination sequence, wherein said transcription termination sequence comprises a polyadenylation sequence; and (iii) an insulator sequence which is about 5 kb in length, wherein the insulator sequence does not:
  (a) comprise any regulatory or enhancer elements;
  (b) produce a functional RNA or protein; or
  (c) cause homology dependent gene silencing of a host gene;

wherein the insulator sequence is located between the first transcription unit and the second transcription unit so as to reduce leaky expression of the lethal nucleic acid caused by the strong constitutive promoter in the second transcription unit.

2. The construct as claimed in claim 1, wherein the lethal gene is selected from the group consisting of barnase, RnaseTI, binase, rolB, rolC and a gene encoding diphtheria toxin A.

3. The construct as claimed in claim 1, wherein the lethal gene is barnase.

4. The construct as claimed in claim 1, wherein the tapetum specific promoter of the first transcription unit is a promoter from a gene selected from the group consisting of TA29, A9, A3, tap1 and bcp1.

5. The construct as claimed in claim 1, wherein the tapetum specific promoter is from a TA29 gene.

6. The construct as claimed in claim 1, wherein the selectable marker gene is a herbicide resistance-conferring gene selected from the group consisting of bar, ALS, and tfda, or an antibiotic resistance-conferring gene selected from the group consisting of nptII, hpt and aadA.

7. The construct as claimed in claim 1, wherein the selectable marker gene is bar.

8. The construct as claimed in claim 1, wherein the strong constitutive promoter is a CaMV35S promoter.

9. The construct as claimed in claim 1, wherein the insulator sequence comprises coding sequences of a topoisomerase gene from pea and an acetolactate synthase gene from Arabidopsis.

10. A male sterile transgenic plant or seeds thereof, wherein the plant or seeds comprise in their nuclear genome the construct of claim 1.

11. The plant as claimed in claim 10, wherein the plant is selected from the group consisting of a dicotyledonous and a monocotyledonous plant.

12. The plant of claim 10, wherein the plant is *Brassica juncea*.

13. A method of producing male-sterile plants of *Brassica juncea*, wherein said method comprises the steps of:

(A) transforming cells of *Brassica juncea* with an insulator construct comprising:
  (i) a first transcription unit comprising in operable linkage: a tapetum specific promoter, a lethal nucleic acid and a transcription termination sequence, wherein said transcription termination sequence comprises a polyadenylation sequence;
  (ii) a second transcription unit comprising in operable linkage: a strong constitutive promoter, a selectable marker nucleic acid and a transcription termination sequence, wherein said transcription termination sequence comprises a polyadenylation sequence; and
  (iii) an insulator sequence which is about 5 kb in length, wherein the insulator sequence does not:
    (a) comprise any regulatory or enhancer elements;
    (b) produce a functional RNA or protein; or
    (c) cause homology dependent gene silencing of a host gene;
  wherein the insulator sequence is located between the first transcription unit and the second transcription unit so as to reduce leaky expression of the lethal nucleic acid caused by the strong constitutive promoter in the second transcription unit;

(B) regenerating transformed plants from the transformed cells;

(C) selecting male-sterile plants from the transformed plants, wherein the male-sterile plants exhibit normal vegetative morphology, normal female fertility, absence of pollen production and failure to set seed on selfing;

(D) selecting from the plants of step (C) male-sterile plants that have a single copy of the insulator construct;

(E) selecting the male-sterile plants from step (D) with untransformed *Brassica juncea* plants to obtain progeny plants; and (F) selecting from the progeny plants of step (E) plants that exhibit normal seed germination frequencies, normal segregation of the selectable marker nucleic acid, and stable inheritance of male sterility.

14. The method as claimed in claim 13, wherein step (A) is carried out by Agrobacterium-mediated transformation using a disarmed Ti plasmid.

* * * * *